(12) United States Patent
Knofe et al.

(10) Patent No.: US 10,267,815 B2
(45) Date of Patent: Apr. 23, 2019

(54) DEVICE FOR POSITIONING VESSELS AND UTILIZATION OF A DEVICE FOR POSITIONING VESSELS

(75) Inventors: Helmut Knofe, Norderstedt (DE); Jens-Peter Kroog, Großhansdorf (DE); Judith Lucke, Hamburg (DE)

(73) Assignee: Eppendorf AG, Hamburg (DE)

( * ) Notice: Subject to any disclaimer, the term of this patent is extended or adjusted under 35 U.S.C. 154(b) by 322 days.

(21) Appl. No.: 13/984,416

(22) PCT Filed: May 30, 2012

(86) PCT No.: PCT/EP2012/002273
§ 371 (c)(1),
(2), (4) Date: Aug. 8, 2013

(87) PCT Pub. No.: WO2013/178235
PCT Pub. Date: Dec. 5, 2013

(65) Prior Publication Data
US 2014/0147922 A1 May 29, 2014

(51) Int. Cl.
*G01N 35/02* (2006.01)
*B01L 9/06* (2006.01)
*G01N 35/00* (2006.01)
*G01N 35/04* (2006.01)

(52) U.S. Cl.
CPC ............. *G01N 35/025* (2013.01); *B01L 9/06* (2013.01); *G01N 2035/0455* (2013.01); *Y10T 436/114165* (2015.01)

(58) Field of Classification Search
CPC ............. B01L 9/06; Y10T 436/114165; G01N 2035/0455; G01N 35/025

USPC .............................................. 436/48; 422/64
See application file for complete search history.

(56) References Cited

U.S. PATENT DOCUMENTS

| 4,276,258 A | 6/1981 | Ginsberg et al. |
| 2007/0189924 A1* | 8/2007 | Knight ............................ 422/63 |

FOREIGN PATENT DOCUMENTS

| EP | 1 278 066 A2 | 1/2003 |
| EP | 1 767 949 A1 | 3/2007 |
| WO | 2010/059569 A2 | 5/2010 |

* cited by examiner

*Primary Examiner* — Rebecca M Fritchman
(74) *Attorney, Agent, or Firm* — Vidas, Arrett & Steinkraus, P.A.

(57) ABSTRACT

A device for positioning vessels, with
a holder for vessels, comprising
 a series of receptacles arranged on a circular line, for a circular ring-shaped vessel chain,
 a central area, arranged within the series of receptacles, and having further receptacles for single vessels containing reagents,
 and means for aligning, and with
a carrier for single vessels, which
 comprises a holding plate in the form of a circular disc or of a part of a circular disc, which has holes for single vessels at certain positions, and which
 has at least one further means for aligning the carrier to the means for aligning the holder in a certain position, wherein in this position, the holes are aligned to certain further receptacles, the remaining further receptacles are covered up by the holding plate, and single vessels filled with reaction liquid can be inserted into the holes and into the further receptacles aligned thereto.

14 Claims, 11 Drawing Sheets

DEVICE FOR POSITIONING VESSELS AND UTILIZATION OF A DEVICE FOR POSITIONING VESSELS

CROSS-REFERENCE TO RELATED APPLICATIONS

This is a national stage application of PCT/EP2012/002273, filed on May 30, 2012, the entire content of which are hereby incorporated by reference.

STATEMENT REGARDING FEDERALLY SPONSORED RESEARCH

Not applicable.

BACKGROUND OF THE INVENTION

The present invention relates to a device for positioning vessels. Further, the present invention relates to a utilization of the device for positioning vessels.

In the preparation of the PCR (Polymerase Chain Reaction), nucleic acid is purified at first. The purification of nucleic acids can take place with the aid of magnetic particles. In doing so, nucleic acid is repeatedly dissolved in special reagents, attached on the magnetic particles and separated from the reagents. It is known to perform the purification with the aid of magnetic particles by means of lab automats. In doing so, the samples to be purified, the necessary reagents and the magnetic particles are provided in vessels on a working surface of the lab automat. They are withdrawn from the vessels by means of a pipette of the lab automat, mixed in vessels and subjected to a magnetic field, in which the separation of the magnetic particles with the attached nucleic acids from the solution takes place. In further processing steps, reagents are taken out by means of the pipette, and new reagents are added in order to conduct a further purification step.

The purified nucleic acid is combined with buffer solution, enzyme solution and in case with salt solution in vessels (synonyms for these different solutions are "reagent" or reagents", "reaction liquid" or "reaction liquids"). It is known to perform even theses preparation steps by means of lab automats. In order to do so, the solutions are provided on the working surface in vessels, and pipetted together with the purified samples into vessels for the PCR. The vessels with the pipetted feed material for the PCR are sealed and put into a thermocycler in which the PCR is performed.

BRIEF SUMMARY OF THE INVENTION

In a known system, a holder in the form of an aluminium block is used for the preparation of samples for PCR, which has a series of receptacles arranged on a circular line, into which a circular ring-shaped chain of single vessels connected to each other (circular ring-shaped vessel chain) is put in. The single vessels of the vessel chain will also be designated as "chain vessels" below. Within the series of receptacles, there is an upward projecting area with further receptacles (single vessel receptacles) for single vessels (unconnected vessels), which contain the different reagents. The projecting area has grooves at the outer circumference, into which projections at the inner circumference of the circular ring-shaped vessel chain engage, so that the chain is arranged in a certain position on the holder. Further, the holder has parallel series with smaller further receptacles for further single vessels beyond the series. The further receptacles receive unconnected single vessels with the reagents. The lab automat pipetts the purified samples and the reagents necessary for the PCR into the vessels of the circular ring-shaped vessel chain which are envisaged for this. In doing so, the control equipment of the lab automat assumes that the necessary reagents are provided within certain further receptacles in single vessels. Depending on which nucleic acid or micro-organisms have to be detected, special kits are used. A kit is a composition of different reagents always in single vessels, which are used in a certain biochemical reaction (for instance, a PCR reaction for the detection of certain nucleic acids or micro-organisms, respectively). In order to achieve that the user puts the respective single vessels with the reagents of the respective kit correctly (i.e. in a certain arrangement) into the receptacles envisaged for them, these further receptacles are marked in a suitable manner.

Such a system is notably marketed by the company Qiagen under the name Rotor-Gene®, and having circular ring-shaped vessel chains under the product name Rotor Disc®.

After the feed materials for the PCR have been pipetted together in the vessels of the circular ring-shaped vessel chain, the user withdraws the single vessels with the reagents from the holder. Further, the user inserts the holder with the circular ring-shaped vessel chain into a sealing apparatus. The circular ring-shaped vessel chain is sealed in the sealing apparatus. Thereafter, the user withdraws the circular ring-shaped vessel chain from the holder. The sealed circular ring-shaped vessel chain is set into the thermocycler, and the holder is used in the lab automat again.

In the known system, the insertion of the single vessels into the holder is sumptuous and prone to errors, because each single vessel must be taken by hand and put into the correct receptacle. Even the withdrawal of the single vessels from the receptacles after the removal of the sealed circular ring-shaped vessel chain from the holder is sumptuous, because each single vessel must be taken individually by the hand.

Starting from this, the present invention is based on the goal to provide a device for positioning vessels and a utilization of the device for positioning vessels which reduces the expense of work and the error risk in the preparation of PCR.

The device for positioning vessels according to the present invention has
a) a holder for vessels, comprising
  a series of receptacles arranged on a circular line, for a circular ring-shaped vessel chain,
  a central area, arranged within the series of receptacles, and having further receptacles (single vessel receptacles) for single vessels containing reagents, and
  means for aligning, and
b) a carrier for single vessels, comprising
  a holding plate in the form of a circular disc or of a part of a circular disc, which has holes for single vessels at certain positions, and
  at least one further means for aligning the carrier to the means for aligning the holder in a certain position, wherein in this position, the holes are aligned to certain further receptacles, the remaining further receptacles are covered up by the holding plate, and single vessels filled with reaction liquid can be inserted into the holes and into the further receptacles aligned thereto.

The device of the present invention comprises a holder for vessels and a carrier for single vessels. The holder for vessels is equipped with a series of receptacles on a circular line for a circular ring-shaped vessel chain. Further, the holder has an area arranged within the series of receptacles with further receptacles for single vessels containing reagents. Moreover, the holder has means for aligning.

The carrier for single vessels comprises a holding plate in the form of a circular disc or of a part of a circular disc with holes for single vessels at certain positions. The carrier is provided with further means for aligning the carrier to the means for aligning the holder. When the further means for aligning are aligned to the means for aligning, the carrier is in a position in which the holes are aligned to certain further receptacles, and the remaining further receptacles are covered up by the holding plate. In this position, single vessels filled with reaction liquid can be inserted into the holes and the further receptacles aligned thereto.

In the device of the present invention, the carrier can be equipped with single vessels before it is aligned to the holder. The carrier is only provided with holes for single vessels with reagents, which are necessary for the preparation of feed materials for the individual biochemical reaction to be carried out, a PCR for instance. The inserted single vessels project from the bottom side of the holding plate. The single vessels can be easily put into the further receptacles of the holder by aligning the carrier to the holder. When the single vessels are arranged in the further receptacles, the carrier rests on the holder. Alternatively, the carrier is at first put onto the holder, by aligning the further means for aligning to the means for aligning. Thereafter, the carrier is equipped with the single vessels. In both alternatives, the holding plate covers up those further receptacles which are not to be equipped with single vessels containing reagents. The danger of erroneous equipment of the further receptacles with single vessels containing different reagents is reduced through this. However, there is the possibility to equip the holder with single vessels which contain reagents of different kits. In order to do this, the user uses preferably different carriers, with are provided with holes at certain positions for the respective kit to be used, so that the single vessels with the respective reagents to be used are put into the envisaged further receptacles. But in principle it is also possible that the user may equip the holder without a carrier with single vessels which contain reagents of another set. Thus, the user can use the carrier as a matrix for equipping the holder. The work expense for the equipment of the holder with the envisaged single vessels at the envisaged position, and the risk of erroneous equipment are significantly reduced.

Moreover, the carrier can be used for withdrawing the single vessels from the further receptacles. In order to do this, the carrier with the single vessels already put into the holes is lifted. When the single vessels are emptied completely, they can be dumped out of the carrier in a simple manner. Putting in and drawing out the single vessels by means of the carrier implies that the single vessels project somewhat over the holes at the edges thereof, so that they do not slip out of the carrier.

The holding plate is preferably in the shape of a circular disc, notably in case that many further receptacles of the holder must be equipped with single vessels. Alternatively, the holding plate has the shape of a part of a circular disc, for instance of an annular disc or a segment of an annular disc, in particular when only few further receptacles of the holder are to be equipped with single vessels.

According to one embodiment, the means for aligning the holder have a protruding projection, circularly surrounding the area with the further receptacles, which has a recess on at least one certain position, and the further means for aligning the carrier have a projection on the edge of the holding plate which can be matchedly inserted into the recess. By the matched insertion of the projection into the recess, the correct alignment of the carrier to the holder is ascertained. In case that the holder has several recesses and the carrier has several projections, these are matched to each other such that the carrier can be aligned to the holder in only one single alignment, in that exactly only one certain projection fits into one certain recess. For this purpose, at least one recess and the projection to be inserted therein may have specific dimensions, and/or the angular distance of adjacent recesses and projections may be differing.

According to a further embodiment, the series of receptacles is formed on a first cylindrical platform of the holder, and the area with the further receptacles and the means for aligning are formed on a second cylindrical platform of the holder, this second platform being formed on the first platform.

According to further embodiments, the further receptacles of the holder are further series of receptacles, which are arranged on concentric circular lines, and the holes of the carrier are also arranged on concentric circular lines.

According to a further embodiment, the further receptacles of the holder and the holes of the carrier are each arranged on three concentric circular lines at a time. According to a further embodiment, 16 further receptacles are arranged on the outer circular line, 10 further receptacles on the middle circular line and four further receptacles on the inner circular line.

According to a further embodiment, the device comprises a detachable covering which covers up the receptacles and the further receptacles at a distance. The covering can cover up the holder and the carrier with inserted single vessels and an inserted circular ring-shaped vessel chain. The covering can be placed on holder and carrier before and/or after the lab automat pipetts the feed material for the PCR into the chain vessels of the vessel chain. The covering protects the single vessels, the vessel chain and the liquids contained therein against contaminations. Before preparing the feed materials, the covering can be taken off, for instance by a gripping equipment of the lab automat, and set down on a parking position of the working surface of the lab automat. After the preparation of the feed materials, the gripper can fetch the covering in the parking position and put it onto holder and carrier.

According to a further embodiment, the first platform has radially projecting ribs on the outer circumference, which engage into lower recesses at the lower edge of the covering that are matched to the ribs. Through this, the covering is securely positioned in a defined position on the holder. By means of a gripper of a lab automat, the covering can be set onto the holder and can be detached from the holder in the vertical direction.

According to a further embodiment, the holder has positioning means at the bottom, for positioning it on at least one workstation of a lab automat for microtiter plates according to the standard of the "American National Standard Institute" (AINSI) or the SBS-Standard (Society for Biomolecular Sciences). The workstations of lab automats are normally matched to the format of microtiter plates according to the AINSI/SBS standard. For this purpose, the base area of the workstations is matched to the outer dimensions of the rectangular base (footprint) of microtiter plates according to ANSI/SBS 1-2004: "Microplates-Footprint Dimension"). These dimensions are 127,676 mm×85.48 mm, even the tolerances being standardized. The base areas of these workstations are limited by stops or other positioning means of the workstations, which ascertain accurate positioning of microtiter plates. In the lab automats of the type EpMotion® of the company Eppendorf AG, the workstations are limited by five pins projecting on their corners from the working area. From these, four pins are fixedly connected to the working area, and one pin is mounted so as to be movable in the direction towards the diagonally opposite corner, and biased towards the opposite corner by a spring. Two pins fixedly connected to the working area exist on the opposite corner. On the further corners, there is only one pin at a time. Near to the corners, the pins that are fixedly connected to the working area bear closely against a microtiter plate that is set onto the workstation. The movable pin bears against a further corner of the microtiter plate. The movable pin facilitates to put the microtiter plate onto the working area, and the removal of it from there. It presses the microtiter plate against the rigid pins, so that it is accurately positioned on the working area.

The holder with the vessels arranged thereon can be positioned directly on at least one workstation. Due to the adaptation of its positioning means to the SBS Standard for microtiter plates, accurate positioning is easily feasible. The user has only to arrange the holder on a workstation by means of the positioning means. The envisioned workstation for positioning the holder is known to the control equipment of the lab automat, so that it can dip the pipette into the respective envisioned vessels.

According to a further embodiment, the positioning means are outer edges of a base of the holder, whose dimensions correspond to the dimensions of at least one workstation of a lab automat for microtiter plates according to the SBS standard.

According to a further embodiment, the holder comprises a base body comprising the receptacles and the further receptacles, and an adapter holding the base body with the positioning means, or the holder is a base body comprising the receptacles. By means of an adapter, the holder can be positioned on one single workstation of a lab automat, even in case that its dimensions exceed or fall below the dimensions of the workstation.

According to a further embodiment, the holding plate of the carrier has at least one certain marking on the top side near to each hole. The marking makes the correct positioning of vessels in the holes easy for the user. According to one embodiment, the marking comprises a colour code, numerals, characters, symbols or a combination of the aforementioned kinds of codes. The single vessels are preferably provided with corresponding codes.

According to a further embodiment, feet that can be put into further receptacles of the carrier for putting the carrier on a ground project from the bottom side of the holding plate, in order to support the holding plate in a distance from the ground, and/or a handle element projects from the upper side of the holding plate. When the carrier is set down on a ground with its feet, single vessels can be put into the holes. The carrier equipped with single vessels can be set into further receptacles of the holder with its feet. Alternatively, the carrier can be set down directly on the holder of the device or on another holder in order to insert single vessels. The feet may be omitted in this case. The handle element facilitates to carry the equipped holder and helps to avoid contaminations of inserted single vessels and liquids contained therein.

According to a further embodiment, the device comprises several carriers, wherein each carrier has a certain specific arrangement of the holes in the holding plate. The different carriers serve to prepare different feed materials for the PCR.

In case that the PCR is to be performed with other feed materials, another holder with a specific arrangement of holes can be used.

According to a preferred embodiment, the arrangement of the holes is optimized such that when the lab automat prepares the feed materials for which the carrier is destined, it travels with the pipette over paths that are as small as possible.

According to a further embodiment, the holder and/or the carrier are made of metal. This favours temperature control of the device. For temperature control, the device can be designed so as to match with a heating and/or cooling station of the lab automat.

Some advantageous utilizations of the device described above are summarized below:

Utilization of a device for positioning vessels:
a circular ring-shaped vessel chain is put into the receptacles of the holder arranged on a circular line,
single vessels filled with reagents are put into the holes of the carrier, wherein single vessels containing certain reagents are put into certain holes,
the carrier with the contained single vessels is aligned to the further receptacles of the holder, and with the further means for positioning to the means for positioning of the holder, and is put up on the holder in the correct position, and
reagents are picked up from certain single vessels, and are filled in certain chain vessels of the vessel chain.

According to one embodiment, the single vessels are put into holes next to which there is at least one marking which gives a sign concerning the reagent which is contained in the respective single vessel that is to be put in.

According to a further embodiment, the holder is positioned on the working surface of a lab automat.

According to a further embodiment, the holder is positioned on a workstation of a lab automat for microtiter plates according to the SBS standard.

According to a further embodiment, the reagents are withdrawn from the single vessels by means of a pipette of the lab automat, and are pipetted into the chain vessels of the circular ring-shaped vessel chain. According to a further embodiment, samples are pipetted into chain vessels of the vessel chain by means of the pipette.

According to a further embodiment, after filling the vessel chain, the carrier with the contained single vessels is detached from the holder, and the carrier is emptied.

According to a further embodiment, the vessel chain is sealed on the holder after having been filled.

The present invention will be explained in more detail by way of the attached drawings of an example of its realisation. In the drawings show:

BRIEF DESCRIPTION OF THE SEVERAL VIEWS OF THE DRAWINGS

FIG. 9 the holding plate of the same carrier in a top view.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated.

In the present application, the designations "top" and "bottom" refer to the arrangement of the device for positioning with the holder on a horizontal floor, and with the carrier on the top of the holder.

Figure 1:
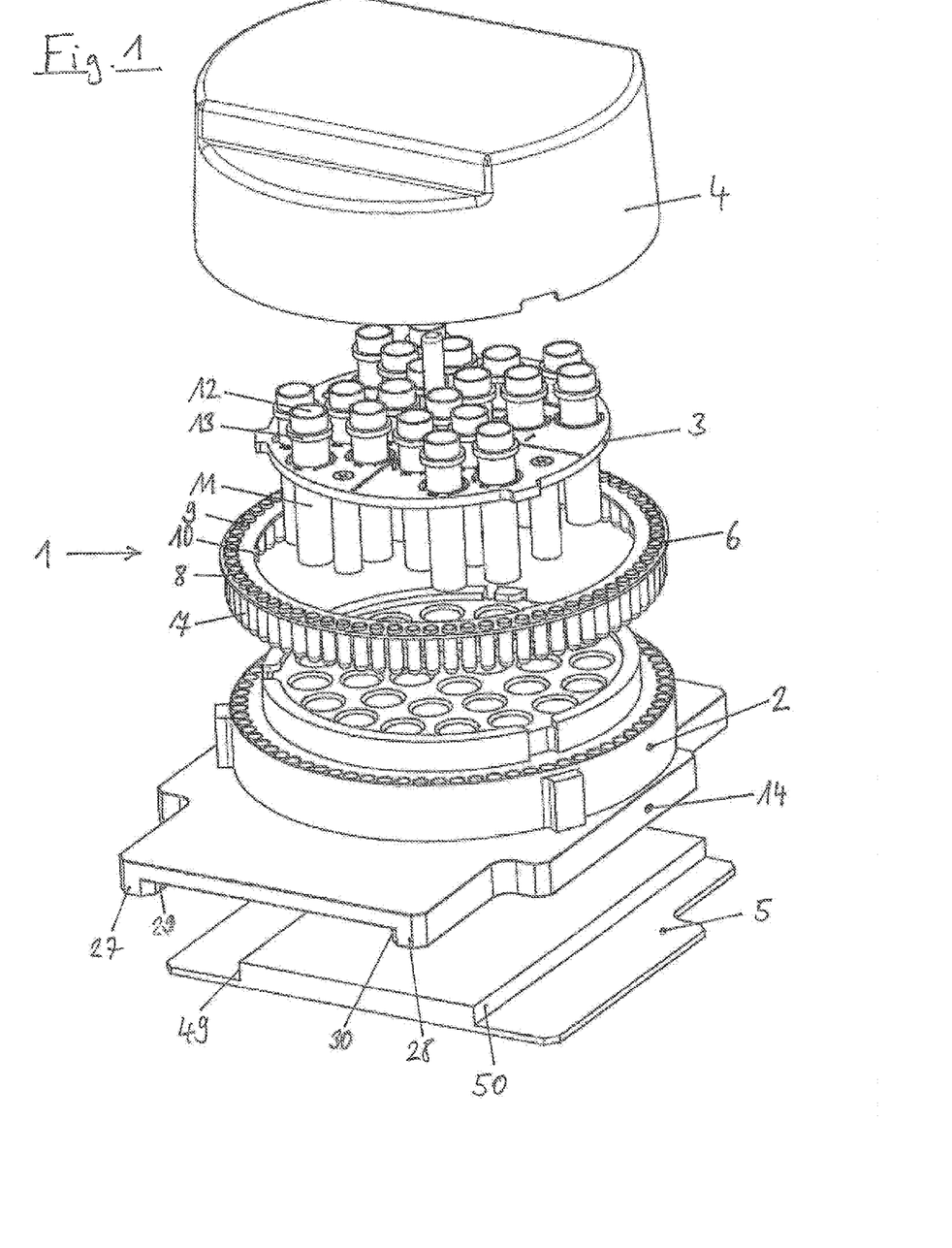
FIG. 1 the device for positioning vessels, with a circular ring-shaped vessel chain and single vessels in a perspective exploded view.

According to FIG. 1, a device for positioning 1 has a holder 2, a carrier 3, a covering 4 and an adapter 5.

Moreover, FIG. 1 shows a circular ring-shaped vessel chain 6 for insertion into the holder 2. The circular ring-shaped vessel chain 6 comprises 72 parallel arranged chain vessels 7, which are connected to each other at their upper edges by a circular ring disc shaped connecting element 8. The individual chain vessels 7 have their chain vessel opening 9 about in the plane of the connecting element 8. The circular ring-shaped vessel chain is marketed by the company Qiagen under the product name Rotor Disc®.

On the inner circumference of the connecting element 8, the circular ring-shaped vessel chain 6 has radially inward projecting inner projections 10. In the circumferential direction of the connecting element 8, the inner projections 10 have different widths and/or have different angular distances from each other. The inner projections 10 are uniformly distributed over the inner circumference of the circular ring-shaped vessel chain 6. Seen in the circumferential direction of the connecting element 8, one inner projection 10 is broader than the two other inner projections 10.

Further, according to FIG. 1, single vessels 11 which are destined to receive reagents are partially inserted into the carrier. All the single vessels 11 have a coincident outer contour. They are circular cylindrical at the outside, and closed by a bottom at the downside. At the top, they have a single vessel opening 12. Somewhat below of the single vessel opening 12, the single vessels 11 have a radially outward projecting, circulating projection 13. The inner contour of the single vessels 11 may vary, so that the single vessels 11 can be filled with different amounts of liquid and in spite of this, the level in the different single vessels 11 remains substantially equal.

Figure 2:
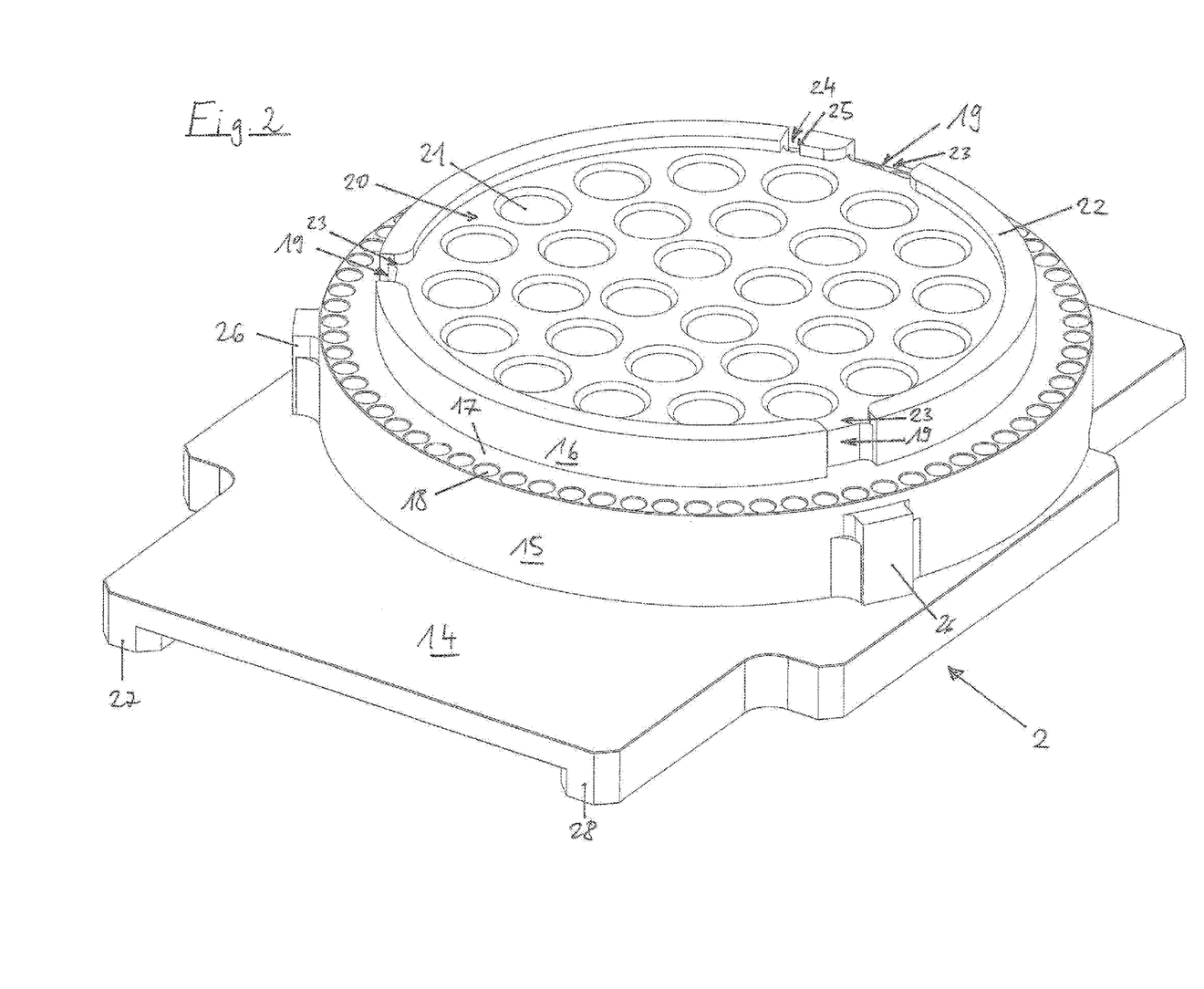
FIG. 2 a holder of the device in a perspective view.
Figure 3:
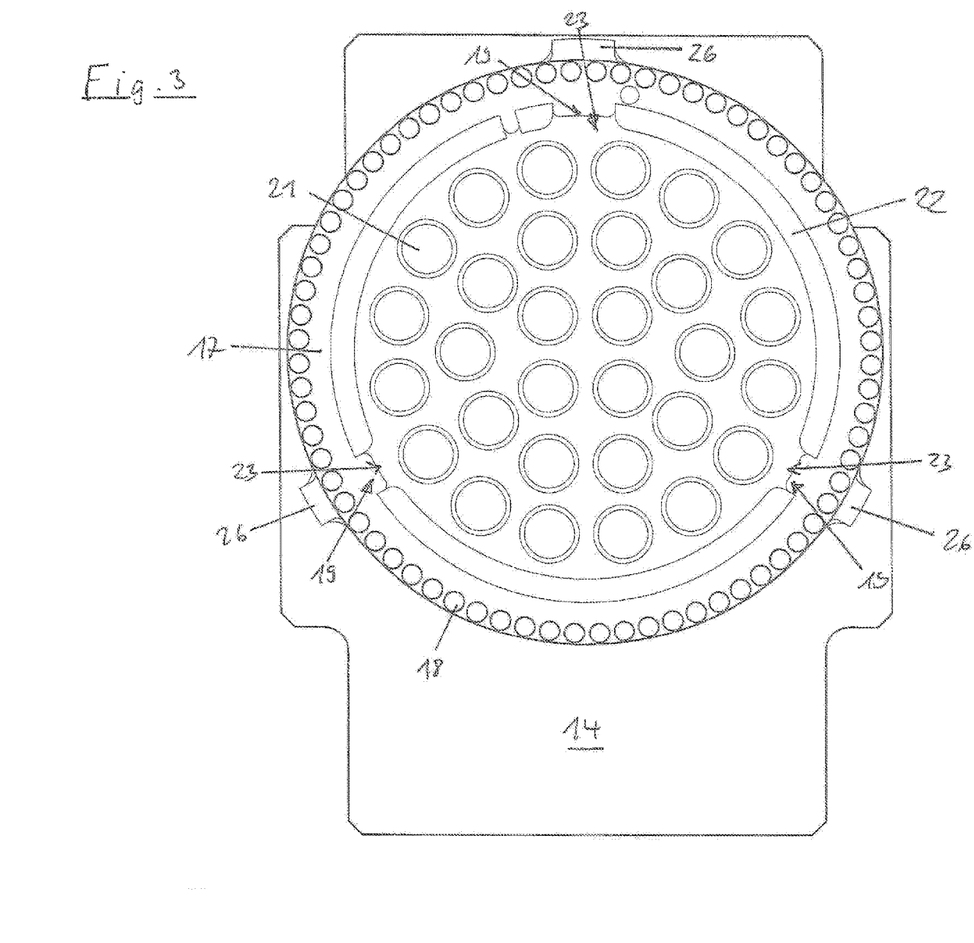
FIG. 3 the same holder in a top view.

According to FIGS. 2 and 3, a holder 2 has a base plate 14 which is cross-shaped when seen from the top. A cylindrical first platform 15 projects from the base plate 14 at the top. A cylindrical second platform 16 projects upwardly from the first platform 15. A horizontal step 17 circulates between the first platform 15 and the second platform 16. A series of receptacles 18 exists on a circular line on the step 17. In the example, there are 72 receptacles. Each receptacle 18 is dimensioned such that it can accommodate one single chain vessel 7 of the circular ring-shaped vessel chain 6.

On the outer circumference of the second platform 16, there are three axially directed grooves 19. These are uniformly distributed over the circumference of the second platform 16. The groove 19 which is at the upside in FIG. 2 is broader than the two other grooves 19. With the inner projections 10, the circular ring-shaped vessel chain 6 can be inserted into the grooves 19 in a certain rotational position, in which the broad inner projection 10 engages in the broader groove 19. In this position, the circular ring-shaped vessel chain 6 with its chain vessels 7 can be put into the receptacles 18.

The second platform 16 is even at the topside. This area 20 of the holder 2 is arranged within the receptacles 18. The area 20 has further receptacles 21. The further receptacles 21 are arranged on three circular lines, which are concentric to each other and to the circle on which the receptacles 18 are arranged. Sixteen further receptacles 21 are arranged on the outer circular line, ten further receptacles 21 on the middle circular line and four further receptacles 21 on the inner circular line.

At the outer edge, the second platform 16 has an upward protruding projection 22, which surrounds the area 20 with the further receptacles 21 like a circular ring. The projection 22 has recesses 23 on three evenly spaced positions directly above the grooves 19. The uppermost recess 23 in FIG. 3 is broader in the circumferential direction of the area 20 than the two further recesses 23. The width of the recesses 23 corresponds to the width of the respective grooves 19 arranged below them.

Next to the uppermost recess 23 in FIG. 3, there is a further recess 24 on the upward protruding projection 22, which is arranged on the circumference of the second platform 16 above a further groove 25. The further recess 24 has a smaller width in the circumferential direction of the second platform 16 than the recesses 23. The width of the further recess 24 corresponds to the width of the further groove 25.

Each further receptacle 21 has a funnel-shaped countersunk at its edge.

The first platform 15 has three radially outward projecting ribs 26 on its outer circumference. Each rib 26 is directed towards a groove 19 on the circumference of the second platform 16. The width of the ribs 26 in the circumferential direction of the first platform 15 corresponds to the width of the respective groove 19 aligned thereto.

At the bottom, the base plate 14 has projecting stripe-shaped pedestals 27, 28 at the sides which are left and right in FIG. 3.

Further, the base plate 14 has means for connecting 29, 30 to the adapter 5 on the bottom side. For instance, the means for connecting 29, 30 are guiding surfaces 29, 30 at the inner sides of the pedestals 27, 28 of the base plate 14.

Figure 4:
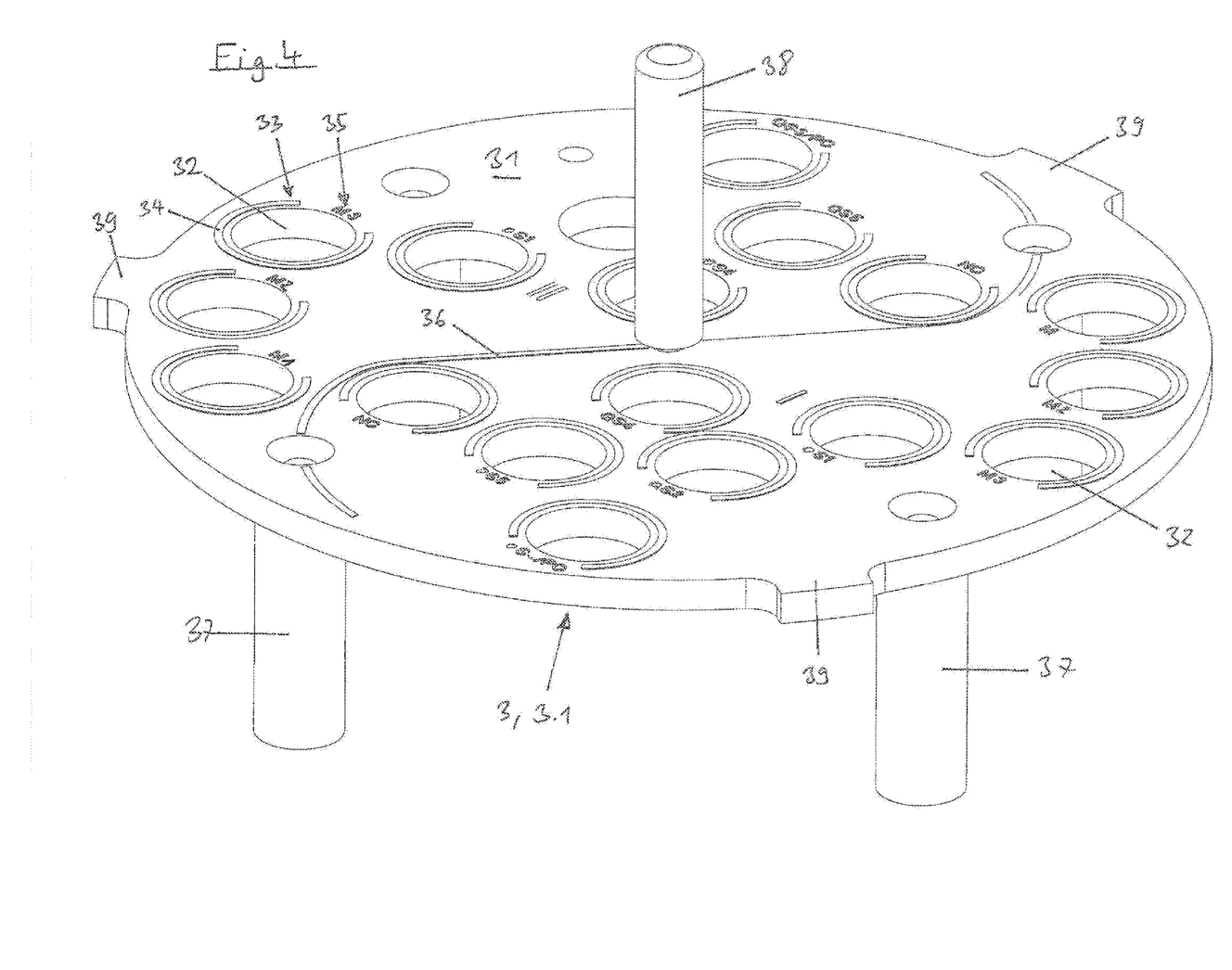
FIG. 4 a carrier of the device in a perspective view.
Figure 5:
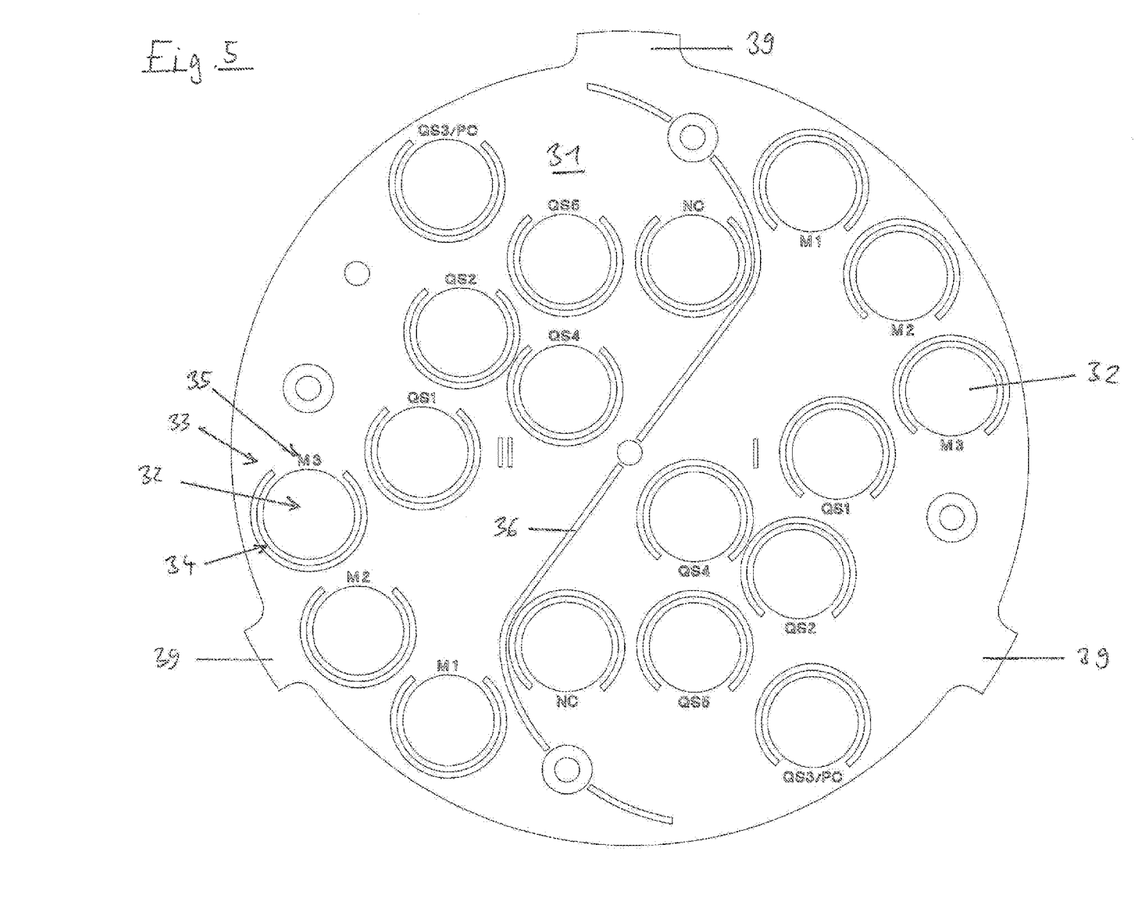
FIG. 5 the holding plate of the same carrier in a top view.

According to FIGS. 4 and 5, the carrier 3.1 has a circular ring-shaped holding plate 31 with holes 32. The holes 32 are arranged in a certain arrangement on three concentric circular lines. The diameter of these circular lines corresponds to the diameters of those circular lines on which the further receptacles 21 of the holder 2 are arranged. The holes 32 of the holding plate 31 can be coincidentally arranged above certain further receptacles 21 of the holder 2. The number of the holes 32 of the holding plate 31 is smaller than the number of the further receptacles 21 of the holder 2, so that upon coincident arrangement of the holes 32 above the further receptacles 24 of the holder, some further receptacles 24 are covered up by the holding plate 31. The arrangement of the holes 32 on the single vessels 31 is matched to the preparation of feed materials for PCR using a special kit of various reagents.

Next to each hole 32, markings 33 are arranged on the upper side of the holding plate 31, which give sign of the reagent which must be contained in a single vessel which is to be inserted.

The markings 33 comprise a colour marking 34 in the form of a colour circle partially enclosing the respective hole, and an alphanumeric marking 35, which is arranged in a gap of the colour marking 34. In the example, holes 32 with same markings 33 are arranged on different sides of a separation line 36 in sectors I and II, so as to be point-symmetric with respect to the centre of the holding plate 31. This makes it easy for the user to equip the holding plate 31 with single vessels 11 which contain reagents that are indicated by the respective markings 33.

Four Feet 37 project downward from the bottom side of the holding plate 31. The feet 37 are arranged at positions below which further receptacles 21 of the holder 2 are situated when the carrier 3.1 is arranged with the holes 32 coincidentally above the further receptacles 21 of the holder 2. The diameter of the feet 37 and the height of the feet 37 are dimensioned such that they can be put into further receptacles 21 and that the holding plate 31 can be set onto the upper side of the further platform 16.

A pin-shaped handle element 38 projects vertically upward from the centre of the holding plate 31.

Outer projections 39 project radially outward from the edge of the holding plate 31. In the example there are three outer projections 39. Neighbouring outer projections 39 have the same angular distance of 120° from each other. The outer projection 39 uppermost in FIG. 5 has a greater width in the circumferential direction of the holding plate 31 than the two other outer projections 39. The width of the outer projections 39 is matched to the width of the recesses 23, so that the outer projection 30 uppermost in FIG. 5 can be matchedly put into the recess 23 uppermost in FIG. 2, and the two other outer projections 39 matchedly into the other recesses 23. Thus, the carrier 3.1 can be set onto the holder 2 in that defined alignment in which the outer projections 39 engage into the recesses 23 in the manner described above, the holes 32 are arranged above certain further receptacles 21 and the feet 37 engage into certain further receptacles 21. The carrier 3.1 with the holding plate 31 can be set on the upper side of the second platform 16 in this alignment. Through this, it is made sure that single vessels 11 set into the holes 32 are inserted into certain further receptacles 21 of the holder 2.

Figure 6:
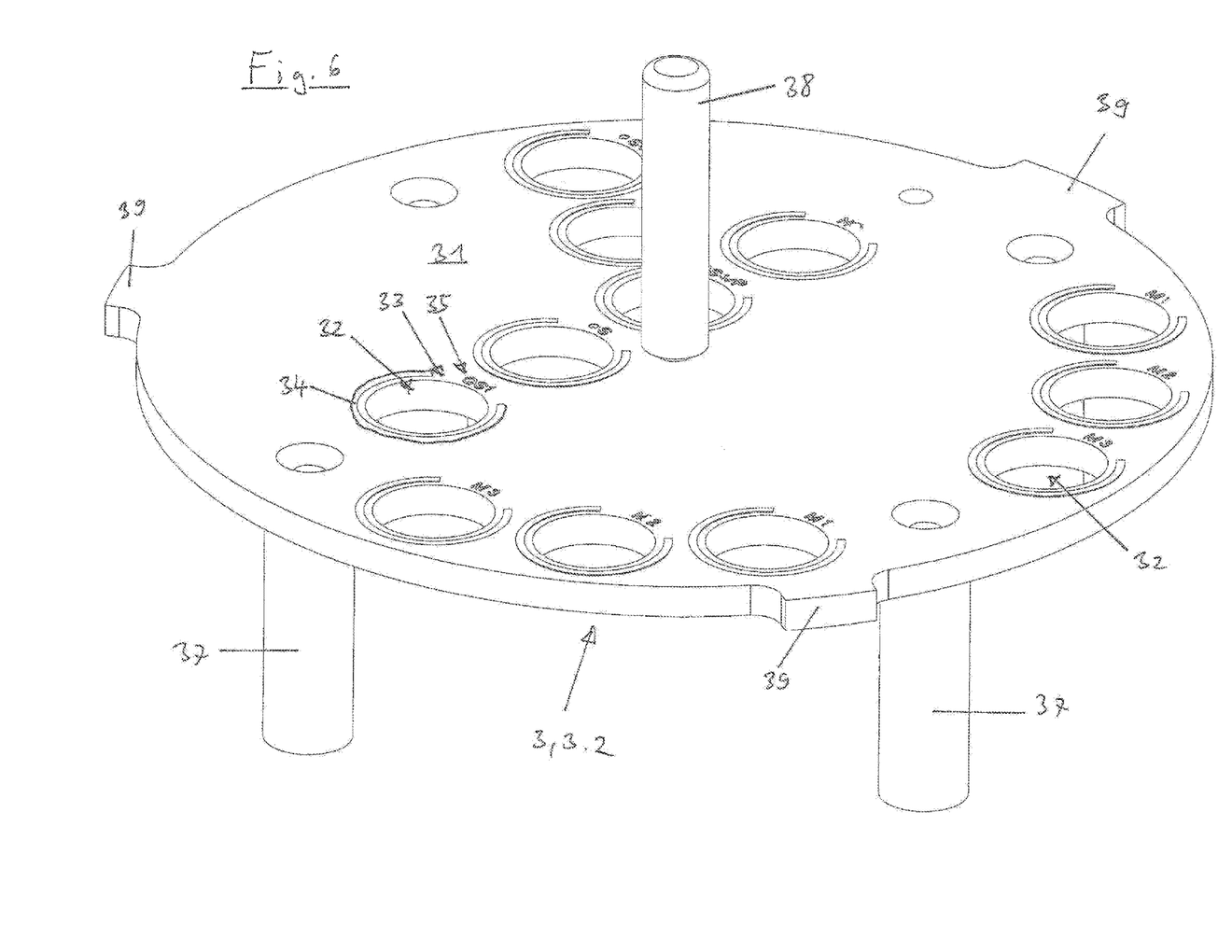
FIG. 6 a further carrier of the device in a perspective view.
Figure 7:
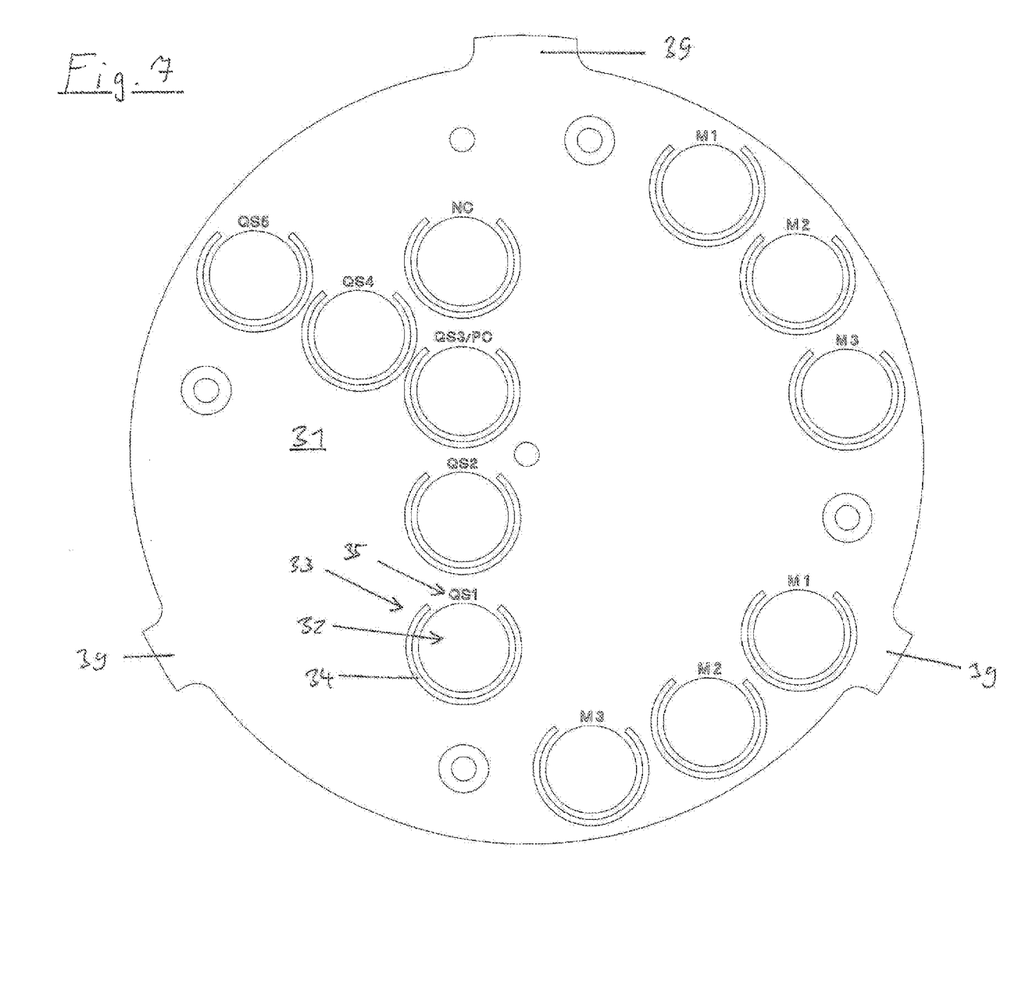
FIG. 7 the holding plate of the same carrier in a top view.

The carrier 3.2 according to FIGS. 6 and 7 differs from the carrier 3.1 described above in that it has another number and arrangement of holes 32 in the holding plate 31. Again, the holes 32 are marked by markings 33 in the form of a colour marking 34 and an alphanumeric marking 35. It can be seen from FIGS. 6 and 7, that there are two groups of holes 32, which have the same markings, so that they are to be equipped in the same manner with single vessels 11 containing various reagents. The remaining holes 32 are to be equipped with further single vessels 11 containing other certain reagents according to their markings 33. This carrier 3 serves for equipping the holder 2 with reagents in single vessels 11 for the preparation of other special feed materials for PCR.

Figure 8:
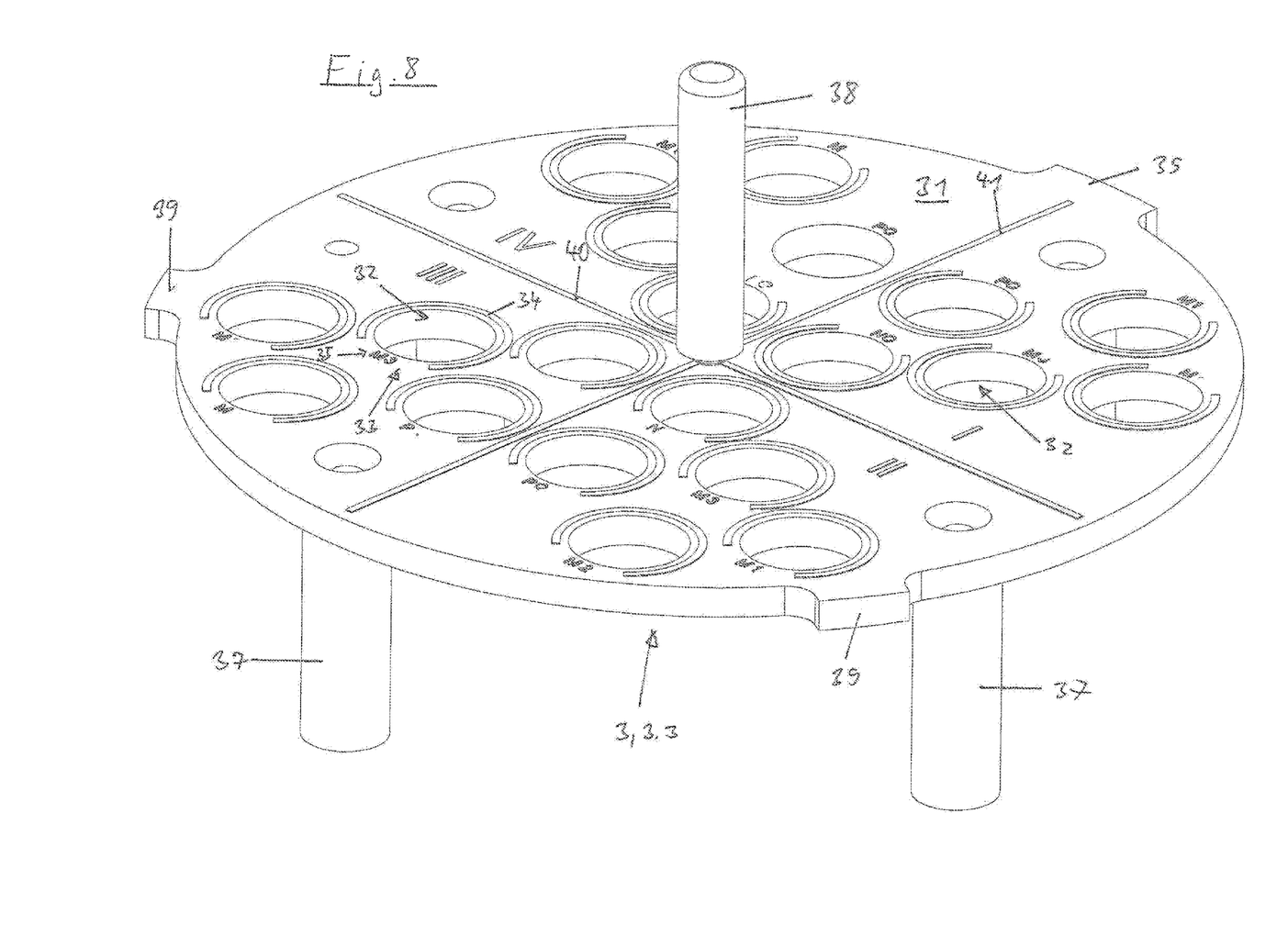
FIG. 8 a further carrier of the device in a perspective view.

The carrier 3.3 according to FIGS. 8 and 9 differs from the carriers 3.1, 3.2 described above also by the number and arrangement of the holes 32 in the holding plate 31. Again, markings 33 in the form of a colour marking 34 and an alphanumeric marking 35 are associated to each hole 32. The holding plate 31 is subdivided into four sectors I-IV by two separation axes 40, 42, arranged similar to a system of coordinates with the zero point in the centre of the holding plate 31. In the sectors I-IV, holes 32, which are provided with the same markings 33, are arranged in point-symmetry with respect to the centre of the holding plate 31, and in axial symmetry with respect to the separation axes 40, 41. This makes it easier for the user to equip the holes 32 with single vessels 11 which contain reagents to which the respective markings 33 give sign.

Figure 10:
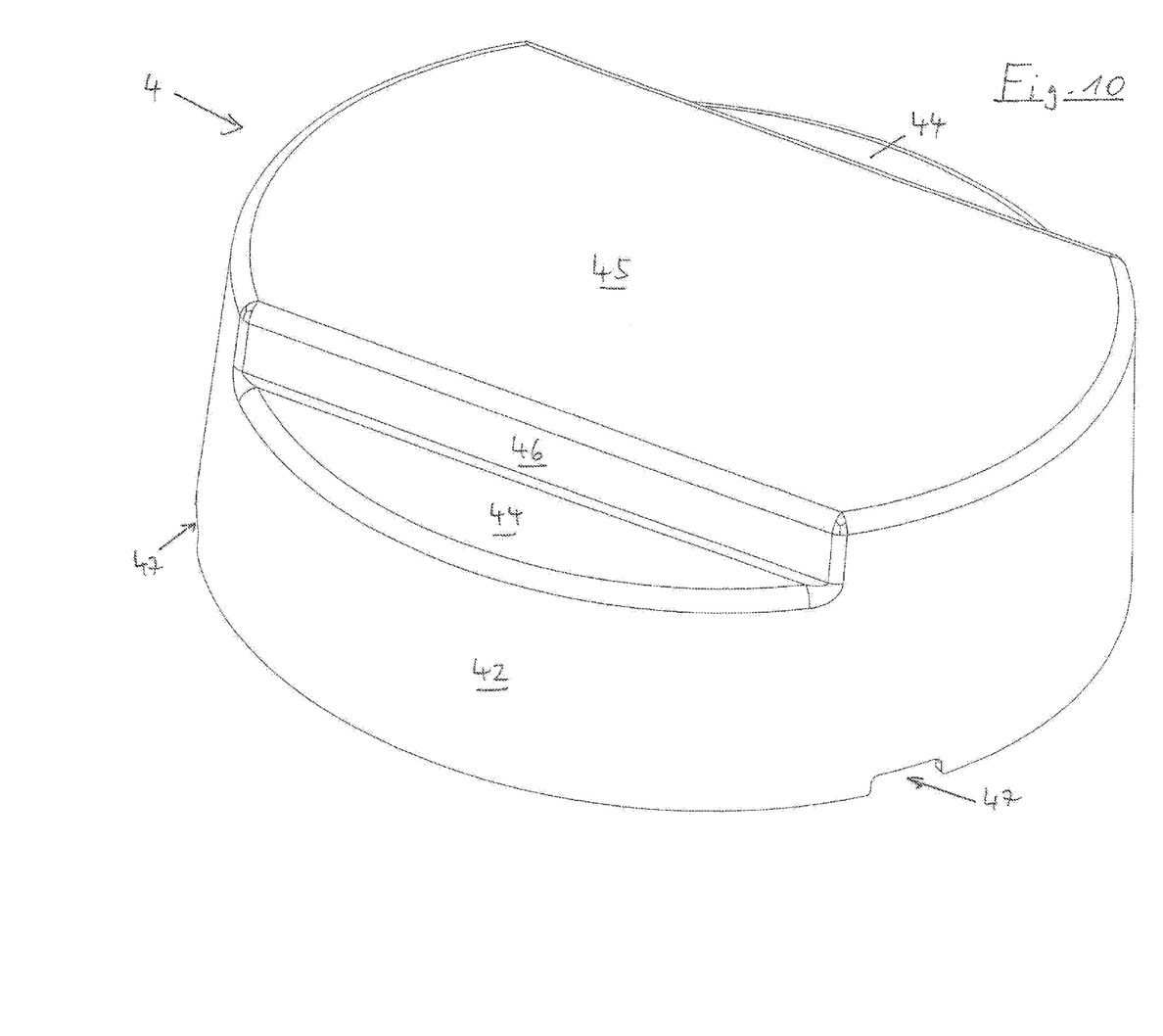
FIG. 10 the covering of the device in a perspective view.

According to FIG. 10, the cap-like covering has a side wall 42, slightly tapering upward in a conical way or being cylindrical, and a cover wall 43. The cover wall 43 has lateral cover wall portions 44 and a central cover wall portion 45, projecting further upward and having lateral flanks 46. The covering 4 can be grasped by a gripper of a lab automat on the lateral flanks 46.

The covering 4 has axially directed lower recesses 47 at the lower edge of the side wall 42. In the example, the covering 4 has in total three lower recesses 47. One lower recess 47 has a width in the circumferential direction of the side wall 42 which corresponds to the width of the broadest rib 26 of the holder 2, which is shown in FIG. 3 at the top side, so that the lower recess 47 can matchedly receive the broadest rib 26. The remaining lower recesses 47 are dimensioned such that they can matchedly receive the remaining ribs 26 of the holder 2. As a consequence, the covering 4 can be set onto the holder 2 only in a certain alignment.

According to FIG. 1, the adapter 5 has a rectangular adapter plate 48, whose outer dimensions correspond to the outer dimensions of the base area of a microtiter plate according to SBS standard. Further, the adapter 5 has further means for connecting 49, 50 in the form of lateral surfaces on a pedestal, which are supported by the guiding surfaces 29, 30 of the holder 2. Moreover, the adapter 5 may comprise pins which can be inserted into bores on the bottom side of the base body 14.

The adapter 5 can be detachably connected to the holder 2 by connecting the further means for connecting 49, 50 to the means for connecting 29, 30. Further, the holder 2 can be positioned on a workstation of the lab automat by means of the adapter 5.

The holder 2 is preferably made of metal, of aluminium in particular. Further preferably, the holder 2 is a single-piece component.

The carrier 3 and/or the adapter 5 are preferably made of a metal, preferably also of aluminium. The holding plate 31 as well as the feet 37 and the handle element 38 or the adapter plate 48 and the pins are preferably produced separately and assembled together.

The covering 4 is preferably made of a plastic material. Further preferably, the covering 4 is injection moulded. Further preferably, the covering is made of a transparent plastic material.

Figure 11:
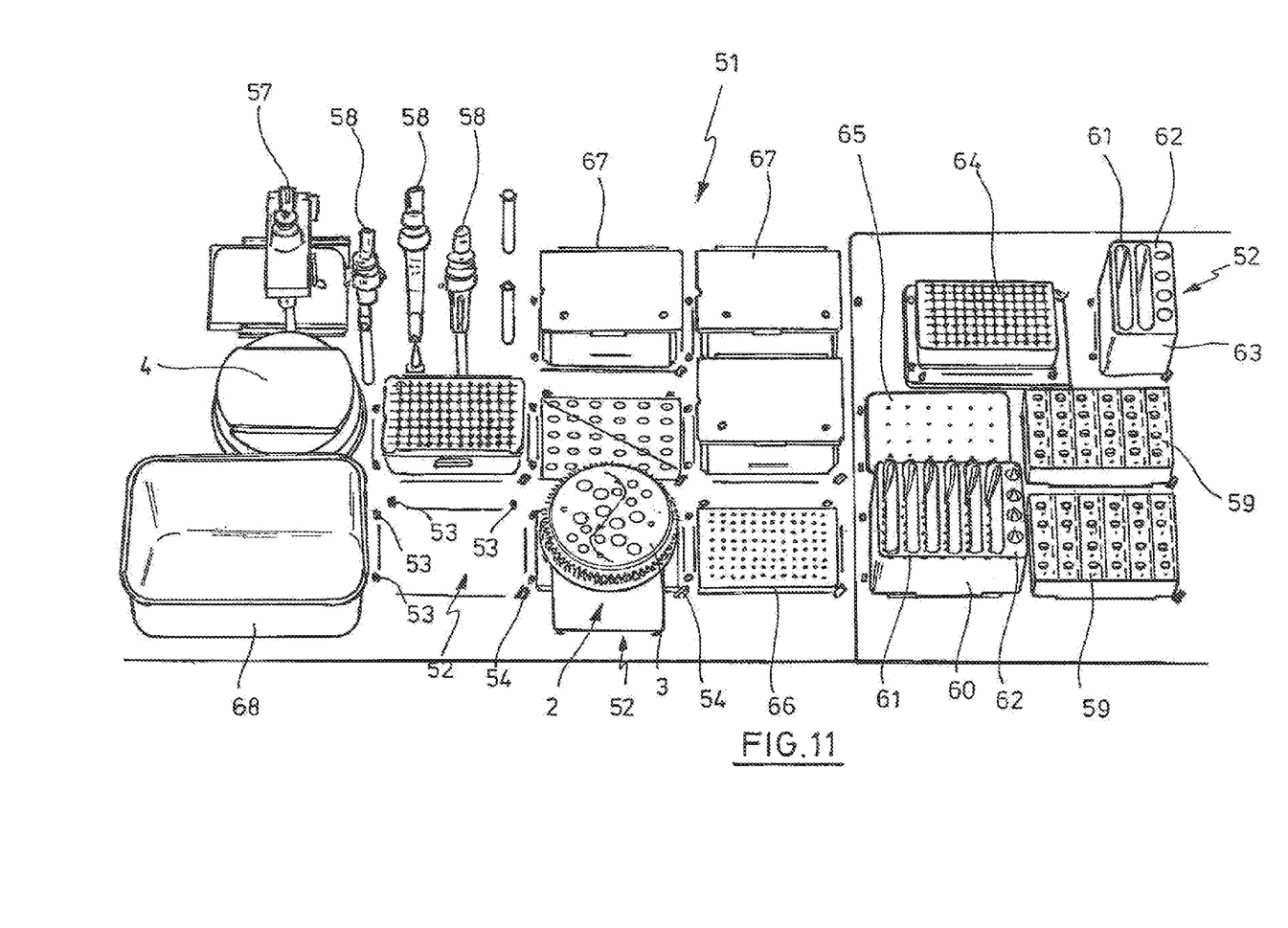
FIG. 11 the working area of a lab automat, equipped with devices for preparing samples for PCR, in a perspective view.

According to FIG. 11, there are several workstations 52 for microtiter plates according to SBS standard on a working surface 51 of a lab automat. Each workstation 52 is limited by four pins 53, fixedly connected to the working surface 53, and one movable pin 54.

Next to one corner, each workstation 52 has two pins 53, fixedly connected to the working surface 51, and one movable pin 54 on a diametrically opposite corner, which is loaded in the direction to the pins 53 by means of a spring and can be moved away from the pins 53 against the action of the spring. Next to the two further corners of each workstation 52, one further pin 53 is arranged at a time, which is fixedly connected to the working surface 51. In addition, the working surface 51 has a further workstation 55 which has a corresponding arrangement of fixedly arranged pins 53 and movable pins 54, but occupies only a fraction of the area of a working surface 52 for a microtiter plate according to SBS standards.

At one workstation 52, a holder 2 is arranged, with a carrier 3 of the device for positioning 1 of the present invention being put up on it. The holder 2 is held between the pins 53, 54 by means of an adapter 5. The device for positioning 1 is disposed on a cooled workstation 52 of the lab automat, in order to cool the reagents.

A covering 4 is set down on a parking position 56 of the working surface 51.

A gripper 57 and pipetting tools 58 of a pipette of the lab automat are set down on further parking positions.

On further workstations, there are frames 59 for vessels with samples to be purified.

A vessel holder 60 is positioned on a further workstation 52 and contains different troughs 61 and inserts 62 for accommodating vessels for reagents. A suitably constructed, small vessel holder 63 is positioned on the further workstation 52.

Further, a reaction vessel 64 with a plurality of receptacles for putting it on a thermomixer is arranged on a workstation 52.

In addition, a special vessel 65 with a plurality of receptacles for magnetic separation of magnetic particles with attached nucleic acid from reagents exists on a workstation 52.

The devices 59 to 65 described above serve for the purification of nucleic acids. By the lab automat, the purified nucleic acid is pipetted into a microtiter plate 66, which is arranged on a further workstation 52 next to the device 1 for positioning vessels 11.

In the central area of the working surface, pipette tip holders 67 are arranged in the vicinity of the device 1 for positioning, in which pipette tips are provided which are used in particular for pipetting together samples and reagents in the circular ring-shaped vessel chain 6.

Used pipette tips can be ejected into a waste container 68 by the pipette, which is arranged on a further position of the working surface 51.

After pipetting samples and solutions together in the circular ring-shaped vessel chain 6, the single vessels 11 are withdrawn from the holes 32 and further receptacles 21. The device for positioning 1 is positioned in a sealing apparatus in order to seal the circular ring-shaped vessel chain 6. Thereafter, the circular ring-shaped vessel chain 6 is set into a thermocycler in order to perform the PCR.

This completes the description of the preferred and alternate embodiments of the invention. Those skilled in the art may recognize other equivalents to the specific embodiment described herein which equivalents are intended to be encompassed by the claims attached hereto.

LIST OF REFERENCE SIGNS 1 device for positioning
2 holder
3, 3.1, 3.2, 3.3 carrier
4 covering
5 adapter
6 circularly shaped vessel chain,
7 chain vessel
8 connecting element
9 opening of chain vessel
10 inner projection
11 single vessel
12 opening of a single vessel
13 circumferential projection
14 base plate
15 first platform
16 second platform
17 step
18 receptacle
19 groove
20 area
21 further receptacles
22 upward protruding projection
23 recess
24 further recess
25 further groove
26 rib
27, 28 pedestal
29, 30 means for connecting
31 holding plate
32 hole
33 marking
34 colour marking
35 alphanumeric marking
36 separation line
37 foot
38 handle element
39 outer projection
40, 41 separation axis
42 side wall
43 cover wall
44 lateral cover wall portion
45 centre cover wall portion
46 flank
47 lower recess
48 adapter plate
49, 50 further means for connecting
51 working surface
52 workstation
53 pin
54 movable pin
55 further workstation
56 parking position
57 gripper
58 pipetting tools
59 frames
60 vessel holder
61 trough
62 insert
63 small vessel holder
64 reaction vessel
65 special vessel
66 microtiter plate
67 pipette tip holder
68 waste container

The invention claimed is:

1. A device for positioning vessels, comprising:
   (a) a holder for a plurality of vessels, comprising a first surface having a plurality of first receptacles arranged in a circle, said holder including a second surface having a central area, said central area having a circular shape, said central area being located inside said arrangement of first receptacles, said central area having a set number of second receptacles and said holder having a first alignment member; and
   (b) a carrier, which comprises a holding plate in the form of a circular disc having a plurality of holes and a second alignment member, said second alignment member vertically coupling with said first alignment member for aligning the carrier relative to the holder in a predetermined rotational position, wherein, the number of said plurality of holes of the holding plate is less than said set number of second receptacles, said plurality of holes being aligned with predetermined second receptacles, said holding plate covering other predetermined second receptacles, wherein individual vessels filled with reaction liquid are inserted into the holes of the holding plate and into the predetermined second receptacles, wherein a plurality of said first receptacles receive said plurality of vessels, said plurality of vessels being disposed adjacent and connected to each other forming a vessel chain, said vessel chain comprising a circular ring disc shaped connecting element having a plurality of apertures, said plurality of vessels being disposed in said plurality of apertures of said circular ring disc shaped connecting element.

2. The device according to claim 1, said holding plate comprising an outside, and an edge projecting toward said outside, wherein said first alignment member has a first protruding projection circularly surrounding the central area, said protruding projection having a recess, and wherein the second alignment member is comprised of a second projection on the edge of the holding plate, said second projection extending towards the outside, wherein said second projection is constructed and arranged to be matchedly inserted into the recess upon alignment of said carrier and the holding plate.

3. The device according to claim 1, wherein the first receptacles are formed on a first platform, and wherein the central area is formed on a cylindrical second platform, the second cylindrical platform extending upwardly from the first platform.

4. The device according to claim 1, wherein the second receptacles are arranged in concentric circles on said holder, and the holes (32) are disposed in concentric circles on said carrier.

5. The device according to claim 1, wherein the second receptacles of said holder are arranged in one of three concentric circles in said central area and the holes of said carrier are arranged in one of three concentric circles and each of the three concentric circles of said holes of said carrier are aligned with one of said three concentric circles of said second receptacles of said holder above said central area.

6. The device according to claim 1, further comprising a detachable covering, wherein the carrier and the holder are constructed and arranged for alignment to the covering.

7. The device according to claim 3, further comprising a detachable covering, wherein the first platform has an outer circumference and radially projecting ribs on the outer circumference, said covering having a lower edge, said lower edge having lower recesses, said lower recesses being constructed and arranged to receive said radially projecting ribs upon alignment of said covering to said holder.

8. The device according to claim 1, wherein the holder has a bottom having a positioning adapter, said positioning adapter being constructed and arranged to position the holder on at least one workstation of a lab automat for microtiter plates.

9. The device according to claim 8, said holder further comprising a base, said base having outer edges, wherein the positioning adapter is connected to said outer edges, the outer edges having dimensions which correspond to the dimensions of at least one workstation of a lab automat for microtiter plates.

10. The device according to claim 9, wherein said base has a base body and further wherein said positioning adapter holds the base body.

11. The device according to claim 1, wherein the holding plate has a top side having at least one marking proximate to each hole.

12. The device according to claim 1, wherein said holding plate includes feet which project from a bottom side of the holding plate, said feet supporting the holding plate at a distance from a ground surface, wherein said holding plate further comprises an upper side and a handle element projecting from the upper side.

13. The device according to claim 1, further comprising a plurality of carriers, wherein each of said carriers is configured with a similar or different arrangement of the holes in the holding plate relative to another of said carriers.

14. A device for positioning vessels, comprising:
(a) a holder for a plurality of vessels, comprising a first surface having a plurality of first receptacles arranged in a circle, said holder including a second surface having a central area, said central area having a circular shape, said central area being located interior to said arrangement of said first receptacles, said central area having a set number of second receptacles and said holder having a first alignment member; and
(b) a carrier comprising a holding plate in the form of a circular disc having a plurality of holes and a second alignment member, said second alignment member vertically coupling with said first alignment member for aligning the carrier relative to the holder in a predetermined rotational position, wherein the number of said plurality of holes of the holding plate is less than said set number of second receptacles, said plurality of holes being aligned with predetermined second receptacles, said holding plate covering other predetermined second receptacles, wherein individual vessels filled with reaction liquid are inserted into the holes of the holding plate and into the predetermined second receptacles, wherein a plurality of first receptacles receive said plurality of vessels, said plurality of vessels being disposed adjacent to each other and connected to form a vessel chain, said vessel chain comprising a circular ring disc shaped connecting element having a plurality of apertures, said plurality of vessels being releasably connected to, or integral with, said plurality of apertures of said circular ring disc shaped connecting element.

* * * * *